US012664985B1

(12) United States Patent
Pallakoff et al.

(10) Patent No.: US 12,664,985 B1
(45) Date of Patent: Jun. 23, 2026

(54) SYSTEMS AND METHODS CONFIGURED TO GENERATE OBJECT VESTIGES BASED ON AUDIO INFORMATION CONVEYING NATURAL SPEECH

(71) Applicant: Suki AI, Inc., Redwood City, CA (US)

(72) Inventors: Matt Pallakoff, Mountain View, CA (US); Akshay Kore, Bengaluru (IN); Luis Daniel Mosquera, Burlingame, CA (US); Bahador Saket, Foster City, CA (US); Gaurav Trivedi, Pittsburgh, PA (US)

(73) Assignee: Suki AI, Inc., Redwood City, CA (US)

( * ) Notice: Subject to any disclaimer, the term of this patent is extended or adjusted under 35 U.S.C. 154(b) by 207 days.

(21) Appl. No.: 18/677,518

(22) Filed: May 29, 2024

(51) Int. Cl.
| | |
|---|---|
| *G10L 15/22* | (2006.01) |
| *G10L 15/06* | (2013.01) |
| *G10L 15/18* | (2013.01) |
| *G10L 15/30* | (2013.01) |
| *G16H 10/60* | (2018.01) |

(52) U.S. Cl.
CPC ............ *G10L 15/22* (2013.01); *G10L 15/063* (2013.01); *G10L 15/1815* (2013.01); *G10L 15/30* (2013.01); *G16H 10/60* (2018.01); *G10L 2015/223* (2013.01)

(58) Field of Classification Search
CPC ... G10L 15/22; G10L 15/063; G10L 15/1815; G10L 15/30; G10L 2015/223; G16H 10/60
See application file for complete search history.

(56) References Cited

U.S. PATENT DOCUMENTS

| | | | |
|---|---|---|---|
| 2013/0238312 A1* | 9/2013 | Waibel | G06F 40/117 |
| | | | 704/8 |
| 2021/0265030 A1* | 8/2021 | Kelly | G16H 10/60 |
| 2024/0087700 A1* | 3/2024 | Gnanasambandam | |
| | | | G16H 10/60 |
| 2024/0304339 A1* | 9/2024 | Larusson | G16H 80/00 |

OTHER PUBLICATIONS

Naphade et al., Extracting Semantics from Audiovisual Contentâ The Final Frontier in Multimedia Retrieval, IEEE Transactions on Neural Networks, 2002 (Year: 2002).*

* cited by examiner

*Primary Examiner* — Bhavesh M Mehta
*Assistant Examiner* — Eunice Lee
(74) *Attorney, Agent, or Firm* — Esplin & Associates, PC

(57) ABSTRACT

Systems and methods configured to generate object vestiges based on audio information conveying natural speech are disclosed. Exemplary implementations may: obtain audio information captured by a client computing platform; provide the audio information to a trained intent recognition model, wherein the trained intent recognition model is trained to determine one or more semantic objects based on the audio information and subsequently determine object vestiges based on the one or more semantic objects, wherein the semantic objects indicate entities and have intent types, wherein the intent types include a content type and a directive type, wherein the entities are spoken by the participants or referred to by the participants; obtain, from the trained intent recognition model, the object vestiges; and store the object vestiges to an electronic record of the subject.

16 Claims, 3 Drawing Sheets

SYSTEMS AND METHODS CONFIGURED TO GENERATE OBJECT VESTIGES BASED ON AUDIO INFORMATION CONVEYING NATURAL SPEECH

FIELD OF THE DISCLOSURE

The present disclosure relates to systems and methods configured to generate object vestiges based on audio information conveying natural speech.

BACKGROUND

During a caregiver-subject interaction, the caregiver and the subject may be discussing matters that require effectuation of actions by the caregiver so that proper care may be provided to the subject. Each of the actions may require extensive manual user input by the caregiver during or after the caregiver-subject interaction.

SUMMARY

One aspect of the present disclosure relates to a system configured to generate object vestiges based on audio information conveying natural speech. The system may include one or more electronic storages, one or more hardware processors configured by machine-readable instructions, and/or other components. The machine-readable instructions may include one or more instruction components. The instruction components may include computer program components. The instruction components may include one or more of information obtaining component, model utilization component, vestige utilization component, presentation component, and/or other instruction components.

The information obtaining component may be configured to obtain audio information captured by a client computing platform. The audio information may convey conversational speech from participants about a subject or topics.

The model utilization component may be configured to provide the audio information and/or other information to a trained intent recognition model. The trained intent recognition model may be trained to determine one or more semantic objects based on the audio information and/or other information input to such model. The trained intent recognition model may be trained to subsequently determine object vestiges based on the one or more semantic objects. The semantic objects may indicate entities and have intent types. The intent types may include a content type, a directive type, and/or other intent type. The entities may be spoken by the participants or referred to by the participants.

The model utilization component may be configured to obtain, from the trained intent recognition model, the object vestiges. Individual ones of the object vestiges may be one of the intent types. The object vestiges of the content type may include content related the subject and the entities. The object vestiges of the directive type may include one or more values to one or more directive parameters related to the entities for external resources to initiate actions for the subject.

The vestige utilization component may be configured to store the object vestiges to an electronic record of the subject and/or transmit such object vestige to one or more external resources.

As used herein, the term "obtain" (and derivatives thereof) may include active and/or passive retrieval, determination, derivation, transfer, upload, download, submission, and/or exchange of information, and/or any combination thereof. As used herein, the term "effectuate" (and derivatives thereof) may include active and/or passive causation of any effect, both local and remote. As used herein, the term "determine" (and derivatives thereof) may include measure, calculate, compute, estimate, approximate, generate, and/or otherwise derive, and/or any combination thereof.

These and other features, and characteristics of the present technology, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of 'a', 'an', and 'the' include plural referents unless the context clearly dictates otherwise.

DETAILED DESCRIPTION

Figure 1:
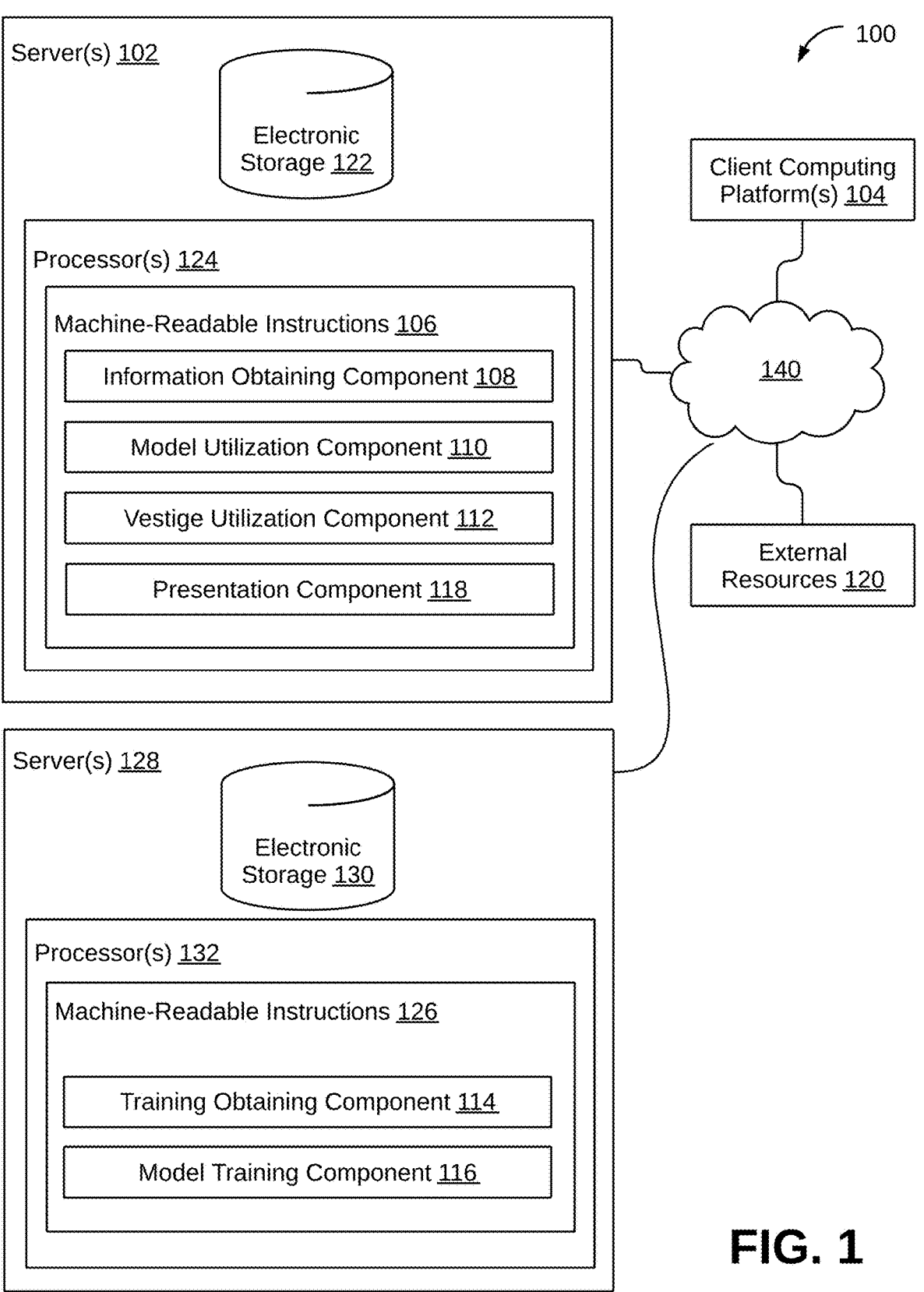
FIG. 1 illustrates a system configured to generate object vestiges based on audio information conveying natural speech, in accordance with one or more implementations.

FIG. 1 illustrates a system 100 configured to generate object vestiges based on audio information conveying natural speech, in accordance with one or more implementations. In some implementations, system 100 may include one or more servers 102, electronic storage 122, servers 128, electronic storage 130, and/or other components. Server(s) 102 may be configured to communicate with one or more client computing platforms 104 via network 140 according to a client/server architecture and/or other architectures. Client computing platform(s) 104 may be configured to communicate with other client computing platforms via server(s) 102 and/or according to a peer-to-peer architecture and/or other architectures. Users may access system 100 via client computing platform(s) 104.

Electronic storage 130 may be similar to electronic storage 122 described herein, but included in server(s) 128. In some implementations, electronic storage 130 and electronic storage 122, and the respective server(s) 102 and 128, may communicate via network 140 or may be the same storage media, and thus store the same information. Electronic storage 130 may store an intent recognition model, training information, and/or other information.

The training information may include audio information representing conversational speech and/or transcripts corresponding to the audio information, entities included in the audio information and/or the transcripts, intent types, final object vestiges, and/or other training information. The intent types may include a content type, a directive type, and/or other intent types. An intent type may represent a purpose conveyed by one or more of the participants determined based on the transcripts, the audio information, and/or other information.

In some implementations, the entities may be categorized into different entity classes. The entity classes may be different sets of related features and parameters that may be discussed during a conversational speech or otherwise uttered, in some implementations, included in notes. The notes may include medical notes, legal notes, mechanical notes, and/or notes specific to other knowledge domains. The entity classes and notes described herein may be related to the medical knowledge domain for exemplary purposes and is not intended to be limiting. The medical knowledge domain may refer to terms, phrases, entities, literature, transcripts, values, and/or other information that are related to medicine. However, other knowledge domains may be utilized additionally or alternatively such as education, auto mechanics, among others.

By way of non-limiting example, the entity classes may include at least complaints, allergies, conditions, medications, procedures, medical devices, appointments, people, caregivers, body parts, and/or other entity classes. In some implementations, the entity classes stored may be modified by the users adding and/or removing one or more entity classes via client computing platforms 104. Individual ones of the entities may be of individual entity classes.

The intent recognition model may be trained to determine semantic objects that indicate the entities and have one of the intent types. Subsequently, the intent recognition model may be trained to determine object vestiges based on the semantic objects. The semantic objects of the content type may be information that indicates content to be generated based on the entities present in the transcripts and/or the audio information. The semantic objects of the directive type may indicate directives to be sent to external resources 120 based on the entities present in the transcripts and/or the audio information. The directives may order, request, or modify medications, devices, appointments, and/or other directives.

Subtypes of the content types may include a clinical note, directions, a summary, a follow up note, a letter, and/or other content subtypes. By way of non-limiting example, the letter may include a referral letter, a thank you letter, an occupational note, an approval letter, and/or other letter. In some implementations, the summary may be of the conversational speech and may include subject instructions. The referral letter may include a name, a title, qualifications, a location, a rate, and/or other information about another user. The occupational note may describe the conditions, the illnesses, the medications, and/or other information related to the subject. The approval letter may specify approval or confirmation of particular conditions, medications, and/or other information about the subject so that the subject is approved for a particular action and/or use. Individual pieces of content included in the object vestiges may be one of the content subtypes and may, itself, be the clinical note, the directions, the summary, the follow up note, the letter, among others. Actions may include ordering prescriptions, ordering imaging, ordering devices, scheduling visits, modifying prescriptions, modifying devices, modifying scheduled visits, and/or other actions.

Subtypes of the directive types may include prescription orders, device orders, imaging orders, visit scheduling, prescription modifications, device modifications, scheduled visit modifications, and/or other directives that system 100 and/or external resources 120 may execute. The directives themselves may include requests that specify values to one or more directive parameters. By way of non-limiting example, the directive parameters may include prescription parameters, to scheduling parameters for visits, imaging parameters, device parameters, and/or other directive parameters, further described herein, where values to such initiate the actions for the subject.

Individual ones of the final object vestiges, and the determined object vestiges, may be one of the intent types. A given object vestige may be a result caused or generated based on a given semantic object. The result may be content generated to be included in a given electronic record, may be a given directive sent to external resources so that one or more items are ordered and obtainable, or other result. The final object vestiges may be instances of object vestiges that were ultimately presented, stored, or otherwise effectuated. The individual final object vestiges may include the content related to the entities, the values to the directive parameters related to the entities to initiate the actions, and/or other information that facilitates effectuating various outcomes. By way of non-limiting example, the final object vestiges may include the notes, the letters, the prescriptions, device information, the directions for the subjects, scheduled appointment information, and/or other information that facilitates the outcomes. The outcomes may, by way of non-limiting example, be the content itself, final distribution of the prescriptions, final distribution of the devices, and scheduled appointment information itself, among others.

Server(s) 128 that may be configured by machine-readable instructions 126 of processor(s) 132. Machine-readable instructions 126 may include one or more instruction components. As described herein, server(s) 128 may be similar to server(s) 102, machine-readable instructions 126 may be similar to machine-readable instructions 106, and processor(s) 132 may be similar to processor(s) 124, but executed by server(s) 128. The instruction components may include one or more of training obtaining component 114, model training component 116, and/or other instruction components.

In some implementations, components 114 and/or 116 may be included as machine-readable instructions 106, therefore the functionality of all the components are executed by server(s) 102. In some implementations, components 108, 110, 112, and/or 118 may be included as machine-readable instructions 126, therefore the functionality of all the components are executed by server(s) 128.

Training obtaining component 114 may be configured to obtain the training information from electronic storage 130 and/or other storage. Training obtaining component 114 may be configured to obtain the intent recognition model from electronic storage 130 and/or other storage. The intent recognition model may be trained to determine semantic objects that are anticipated by the individual transcripts and/or the audio information based on at least the individual transcripts and/or the audio information that are input to the trained intent recognition model, and determine object vestiges based on the semantic objects. Trained intent recognition model may be the same as the intent recognition model but subsequent to training as described.

Model training component 116 may be configured to train the intent recognition model to determine the semantic objects, and thus, the object vestiges, by using at least the audio information and/or the transcripts, the entities, and the intent types, as training input. In some implementations, the training inputs may include electronic records associated with individual subject. The electronic records may be stored in electronic storage 130, 122, and/or other electronic storage that is accessible by components 114 and/or 116. Thus, determining the semantic object may be based on the electronic records. Furthermore, the final object vestiges and/or other training information may be used as the training outputs. The training inputs and the training outputs may be information that are closely correlated. That is, for example, a reoccurring training input, e.g., particular entities identified in the transcripts, may correspond to a training output that occurs often, e.g., a particular final object vestiges. Thus, such training input and training output may be closely correlated. As such, the intent recognition model is trained to determine the object vestiges, which are one of the intent types, based on transcripts and/or the audio information, and that include content, directives, and/or other information to initiate the actions. The training of the intent recognition model may include employing one or more known or novel machine learning techniques.

Model training component 116 may be configured to store the trained intent recognition model to electronic storage 130, electronic storage 122, and/or other storage. In some implementations, electronic storage 130 and electronic storage 122 may be cloud-based storage and/or resources that processor(s) 124 and 132, and instruction components thereof, may access via network 140. In some implementations, electronic storage 122 and electronic storage 130 may be native to server(s) 102 and 128, respectively, and additional cloud-based storage and/or resources may be utilized to store the information described herein in addition to electronic storage 122 and electronic storage 130. The additional cloud-based storage and/or resources may be accessed via network 140.

Electronic storage 122 may further store the electronic records and/or other information. Individual ones of the electronic records may include identifying information of the individual subjects, current medications, current allergies, current illnesses and conditions, test results, notes related to the individual subjects, and/or other information. In some implementations, the individual electronic medical records may include past procedures, past notes related to the individual subjects, past notes related to the past visits or the past procedures, past notes related to the test results, past medications, past allergies, past illnesses and conditions, and/or other past information about the individual subjects. By way of non-limiting example, electronic storage 130 may store an electronic record for the subject.

Server(s) 102 may be configured by machine-readable instructions 106. Machine-readable instructions 106 may include one or more instruction components. The instruction components may include computer program components. The instruction components may include one or more of information obtaining component 108, model utilization component 110, vestige utilization component 112, and/or other instruction components.

Information obtaining component 108 may be configured to obtain the audio information captured by client computing platform 104. The audio information may include digital audio signals that encode sounds of individual utterances of the participants, a recording of the individual utterances of the participants, and/or other audio information. In some implementations, the sounds conveying the utterances of the participants may be detected by the audio input device, such as a microphone, of client computing platform 104. In some implementations, the sounds may be converted to the digital audio signals by converting analog waves to the digital audio signals by precisely measuring the analog waves at consistent and frequent intervals. The recording of the individual utterances may include a digital file of a reproduction of the digital audio signals that cause the sounds, and thus convey the utterances, the digital audio signals, and/or other recording. In some implementations, information obtaining component 108 may be configured to generate the audio information based on the sounds in response to silence that follows individual ones of the utterances from the different participants, a change in language detected, a change in the participant speaking detected, and/or user input via the user interface elements (e.g., selecting a virtual button). In some implementations, the silence may be for a particular amount of time that may be fixed or modifiable by the users. In some implementations, the audio segments may be stored in electronic storage 122 in association with the subject.

The audio information may convey conversational speech from the participants about a subject. The participants may include a medical provider (e.g., doctor, nurse, physician's assistant), a caretaker (e.g., assisted living caretaker), a parent, a guardian of the subject, a user of client computing platform 104, one or more secondary users of client computing platform 104, an owner, the subject themselves, and/or other participants. In some implementations, the user may be the medical provider, the caretaker, and/or other users that primarily use client computing platform 104. In some implementations, the secondary users may include other medical providers, other caretakers, and/or other users that may use client computing platform 104 in addition to the user. In some implementations, the subject may be person, animal, or other living being. In some implementations, the subject may be an object such as a vehicle, a machine, and/or other object. In some implementations, information obtaining component 108 may be configured to generate a transcript by performing speech recognition techniques on the audio information. The speech recognition techniques may be novel and/or known.

In some implementations, information obtaining component 108 may be configured to receive a request. The request may be received from client computing platform 104 of the user such that specific object vestiges to generate are requested. Such request may be received prior to the conversational speech or during the conversational speech. The request may specify one or more particular subtypes of the content types and/or one or more particular subtypes of the directive types for determining the semantic objects. Thus, determining the semantic objects may be based on the selections, the electronic record of the subject, the user, a purpose of the conversational speech, and/or other information.

In some implementations, presentation component 118 may be configured to effectuate, via client computing platform 104 of the user, presentation of an ordered list including the subtypes of the content types and the subtypes of the directive types that are selectable by the user. As such, the user may be enabled to provide the selections for the request.

The users may be associated with user information. The user information for individual users may define, by way of non-limiting example, a name, credentials, education, experience, a title, a department, contact information, and/or other user information that defines the users. The contact information may include one or more phone numbers, email addresses, office locations, mailing addresses, and/or other contact information.

The purpose of the conversational speech may be specified by the subject and/or other ones of the participants prior to or during the conversational speech. The purpose may be, by way of non-limiting example, a routine exam, examination of a particular issue, a follow up on a particular condition or issue, among others. In some implementations, the purpose may be specified by the subject, the caretaker, guardian, and/or other participant while scheduling the visit via a third-party scheduling assistant that may be configured to communicate with server(s) 102 and/or 128, via a component of system 100. In some implementations, the conversational speech may be during the scheduled visit with the user/caregiver. In some implementations, the scheduled visit may be of a visit type. In some implementations, the visit type may be determined based on the purpose. In some implementations, the visit type may be specified by the subject and/or one of the other participants of the scheduled visit. The visit type may be a follow-up type, an operation type, a routine exam type, an urgent visit, a walk-in visit type, and/or other visit type.

Model utilization component 110 may be configured to provide the audio information and/or the corresponding transcript to the trained intent recognition model. In some implementations, the electronic record of the subject, the subtypes of the content types, the subtypes of the directive types, the selections, the user information, the purpose of the conversational speech, the visit type, and/or other information may be provided and input to the intent recognition model. In some implementations, the audio information, the corresponding transcript, the electronic record of the subject, the subtypes of the content types, the subtypes of the directive types, the selections, the user information, the purpose of the conversational speech, the visit type, and/or other information may be provided and input to the intent recognition model upon the audio information be captured (e.g., during the visit). In response to and based on receiving such information, the trained intent recognition model may determine one or more semantic objects and described herein. Subsequently, the trained intent recognition model may determine one or more object vestiges based on the one or more semantic objects.

Individual ones of the semantic objects determined may indicate particular ones of the entities, have one of the intent types, and/or indicate other information. The entities may be spoken by the participants or referred to by the participants. As previously described, the entities may include, by way of non-limiting example, people, physical items, symptoms, medications, and/or other entities in the entity classes. The semantic objects of the content type may indicate that particular content is to be generated based on the entities. The semantic objects of the directive type may indicate the directives to be sent to external sources. The directives may order, request, or modify prescribed medications, devices, appointments, and/or other directives.

Individual ones of the object vestiges may be one of the intent types which corresponds to the intent types of the semantic objects that the object vestiges are individually based on. The object vestiges may be determined based on the electronic record of the subject, the subtypes of the content types, the subtypes of the directive types, and/or other information input to the trained intent recognition model. That is, based on known information about the subject included in the electronic record, the conversational speech, and the requested content and/or directives, the object vestiges may be determined so that they may be utilized and/or effectuated.

The individual object vestiges may include information that may be utilized to cause presentations via client computing platform 104 or may be transmitted to external resources to initiate the actions, and thus cause the outcomes. The object vestiges of the content type may include the content related the subject and the entities. The content may include, by way of non-limiting example and as described herein, the clinical note, one or more sections for the clinical note, the directions for the subject, the summary, the follow up note, the letter(s), one or more images, one or more videos, informative literature, and/or other content.

The object vestiges of the directive type may include one or more values to the one or more directive parameters related to the entities for external resources 120 to initiate the actions for the subject and cause the outcomes. The directive parameters, for ordering or modifying prescriptions, may include a medication brand name, a generic equivalent name, a medication form, a medication strength, a medication dosage, a frequency of use, an indication to terminal use, an expiration date, refill allowance, refill frequency, and/or other prescription parameters. The directive parameters, for ordering imaging, may include one or more parts of the subject, one or more angles for images, one or more types of imaging (e.g., such values may include ultrasound, magnetic resonance imaging (MRI), etc.), and/or other imaging parameters. The directive parameters, for scheduling visits or modifications thereof, may include a date, a start time, an end time, a location, one or more caregivers/users, and/or other scheduling parameters. The directive parameters, for ordering devices, may include a device name, a device model, a device serial number, a device version, a quantity of devices, and/or other device parameters.

In some implementations, the individual object vestiges may include timing information and/or other information. The timing information may indicate times at which the entities included in the semantic objects corresponding to the object vestiges were spoken. The times may include a date, an hour, a minute, a second, a millisecond, a time zone, and/or other time measurements. The times may be based on the audio information. In some implementations, the timing information may be relative to a beginning of the audio information. In some implementations, the timing information may be a universal time, an epoch time, and/or in accordance with another time measurement.

Model utilization component 110 may be configured to obtain, from the trained intent recognition model, the object vestiges. Upon obtainment of the object vestiges, vestige utilization component 112 may be configured to store the object vestiges to the electronic record of the subject. Storing the object vestiges may include grouping the object vestiges in the electronic record of the subject based on the timing information. That is, the object vestiges that were determined in response to the selections made by the user may be grouped together due to such object vestiges being related, e.g., to the same conversational speech.

In some implementations, presentation component 118 may be configured to effectuate presentation of the object vestiges that are of the content type via client computing platform(s) 104 associated with the users, the secondary users, the subject, and/or the other participants.

In some implementations, vestige utilization component 112 may be configured to transmit the object vestiges to external recipients. By way of non-limiting example, the external recipients may be the subject themselves, one of the other participants, an electronic record system, and/or other external recipients. In some implementations, vestige utilization component 112 may be configured to transmit the object vestiges of the directive type to external resources 120 for effectuation. By way of non-limiting example, external resources 120 may include a scheduling system, a pharmaceutical system, a device distributor, and/or other external resources 120.

In some implementations, vestige utilization component 112 may be configured to receive confirmation, from external resources 120, that the transmitted object vestiges of the directive type were effectuated. In some implementations, the confirmation may include the object vestige, including the timing information. The confirmation may be stored in the electronic record based on the timing information such that the confirmation is grouped with other ones of the object vestiges based on the timing information. In some implementations, a denial or redirection may be received from external resources 120. The denial may indicate that a given object vestige could not be effectuated (e.g., prescription could not be filled). The redirection may indicate that the given object vestige could not be effectuated by a particular external resource 120, and thus was subsequently transmitted to an alternate one of external resources 120.

Figure 3:
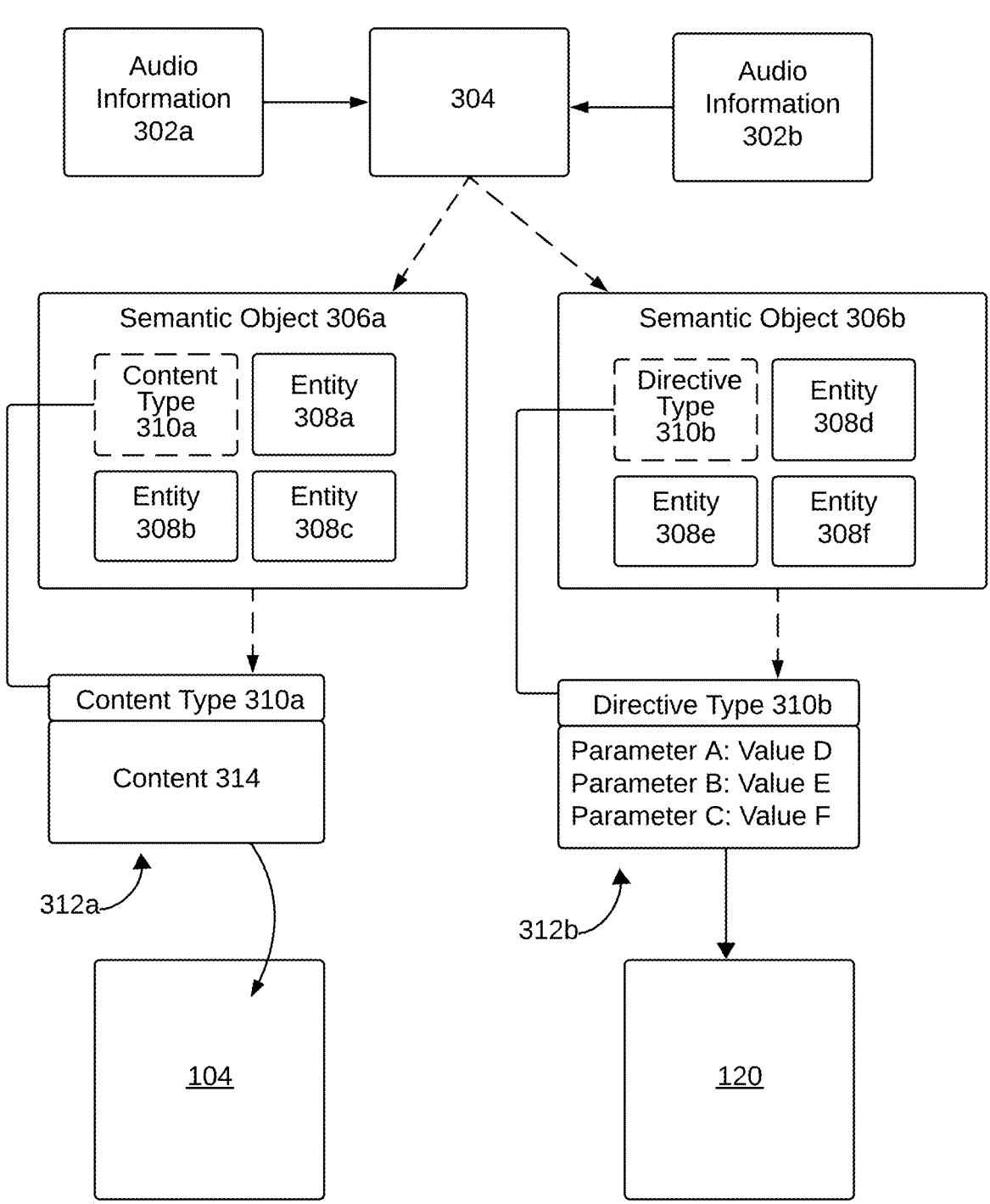
FIG. 3 illustrates an example implementation of the system configured to generate object vestiges based on audio information conveying natural speech, in accordance with one or more implementations.

FIG. 3 illustrates audio information 302 that is provided to trained intent recognition model 304. Trained intent recognition model 304 may be trained to determine semantic objects 306a and 306b. An intent type of semantic object 306a may be content type 310a based on the audio information 302a input to trained intent recognition model 304. Furthermore, semantic object 306a may indicate entities 308a-c based on audio information 302a input to trained intent recognition model 304. Entities 308a-c may have been spoken by participants (not illustrated) and represented by audio information 302a. Based on semantic object 306a, object vestige 312a may be determined by trained intent recognition model 304. Object vestige 312a may be of content type 310a and include content 314. Content 314 may be presented via client computing platform 104.

An intent type of semantic object 306b may be directive type 310b based on the audio information 302b input to trained intent recognition model 304. Furthermore, semantic object 306b may indicate entities 308d-f based on the audio information 302b. Entities 308d-f may have been spoken by participants (not illustrated) and represented by audio information 302b. Based on semantic object 306b, object vestige 312b may be determined by trained intent recognition model 304. Object vestige 312b may be of directive type 310b and include parameter values D-F for parameters A-C, respectively. Object vestige 312b may be transmitted to external resource 120 for effectuation.

Referring to FIG. 1, in some implementations, server(s) 102, client computing platform(s) 104, and/or external resources 120 may be operatively linked via one or more electronic communication links. For example, such electronic communication links may be established, at least in part, via network 140 such as the Internet and/or other networks. It will be appreciated that this is not intended to be limiting, and that the scope of this disclosure includes implementations in which server(s) 102, client computing platform(s) 104, and/or external resources 120 may be operatively linked via some other communication media.

A given client computing platform 104 may include one or more processors configured to execute computer program components. The computer program components may be configured to enable an expert or user associated with the given client computing platform 104 to interface with system 100 and/or external resources 120, and/or provide other functionality attributed herein to client computing platform(s) 104. By way of non-limiting example, the given client computing platform 104 may include one or more of a desktop computer, a laptop computer, a handheld computer, a tablet computing platform, a NetBook, a Smartphone, a gaming console, and/or other computing platforms.

External resources 120 may include sources of information outside of system 100, external entities participating with system 100, and/or other resources. In some implementations, some or all of the functionality attributed herein to external resources 120 may be provided by resources included in system 100.

Server(s) 102 may include electronic storage 122, one or more processors 124, and/or other components. Server(s) 102 may include communication lines, or ports to enable the exchange of information with network 140 and/or other computing platforms. Illustration of server(s) 102 in FIG. 1 is not intended to be limiting. Server(s) 102 may include a plurality of hardware, software, and/or firmware components operating together to provide the functionality attributed herein to server(s) 102. For example, server(s) 102 may be implemented by a cloud of computing platforms operating together as server(s) 102.

Electronic storage 122 may comprise non-transitory storage media that electronically stores information. The electronic storage media of electronic storage 122 may include one or both of system storage that is provided integrally (i.e., substantially non-removable) with server(s) 102 and/or removable storage that is removably connectable to server(s) 102 via, for example, a port (e.g., a USB port, a firewire port, etc.) or a drive (e.g., a disk drive, etc.). Electronic storage 122 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 122 may include one or more virtual storage resources (e.g., cloud storage, a virtual private network, and/or other virtual storage resources). Electronic storage 122 may store software algorithms, information determined by processor(s) 124, information received from server(s) 102, information received from client computing platform(s) 104, and/or other information that enables server(s) 102 to function as described herein.

Processor(s) 124 may be configured to provide information processing capabilities in server(s) 102. As such, processor(s) 124 may include one or more of a digital processor, an analog processor, a digital circuit designed to process information, an analog circuit designed to process information, a state machine, and/or other mechanisms for electronically processing information. Although processor(s) 124 is shown in FIG. 1 as a single entity, this is for illustrative purposes only. In some implementations, processor(s) 124 may include a plurality of processing units. These processing units may be physically located within the same device, or processor(s) 124 may represent processing functionality of a plurality of devices operating in coordination. Processor(s) 124 may be configured to execute components 108, 110, 112, 114, 116, and/or 118, and/or other components. Processor(s) 124 may be configured to execute components 108, 110, 112, 114, 116, and/or 118, and/or other components by software; hardware; firmware; some combination of software, hardware, and/or firmware; and/or other mechanisms for configuring processing capabilities on processor(s) 124. As used herein, the term "component" may refer to any component or set of components that perform the functionality attributed to the component. This may include one or more physical processors during execution of processor readable instructions, the processor readable instructions, circuitry, hardware, storage media, or any other components.

It should be appreciated that although components 108, 110, 112, 114, 116, and/or 118 are illustrated in FIG. 1 as being implemented within a single processing unit, in implementations in which processor(s) 124 includes multiple processing units, one or more of components 108, 110, 112, 114, 116, and/or 118 may be implemented remotely from the other components. The description of the functionality provided by the different components 108, 110, 112, 114, 116, and/or 118 described below is for illustrative purposes, and is not intended to be limiting, as any of components 108, 110, 112, 114, 116, and/or 118 may provide more or less functionality than is described. For example, one or more of components 108, 110, 112, 114, 116, and/or 118 may be eliminated, and some or all of its functionality may be provided by other ones of components 108, 110, 112, 114, 116, and/or 118. As another example, processor(s) 124 may be configured to execute one or more additional components that may perform some or all of the functionality attributed below to one of components 108, 110, 112, 114, 116, and/or 118.

Figure 2:
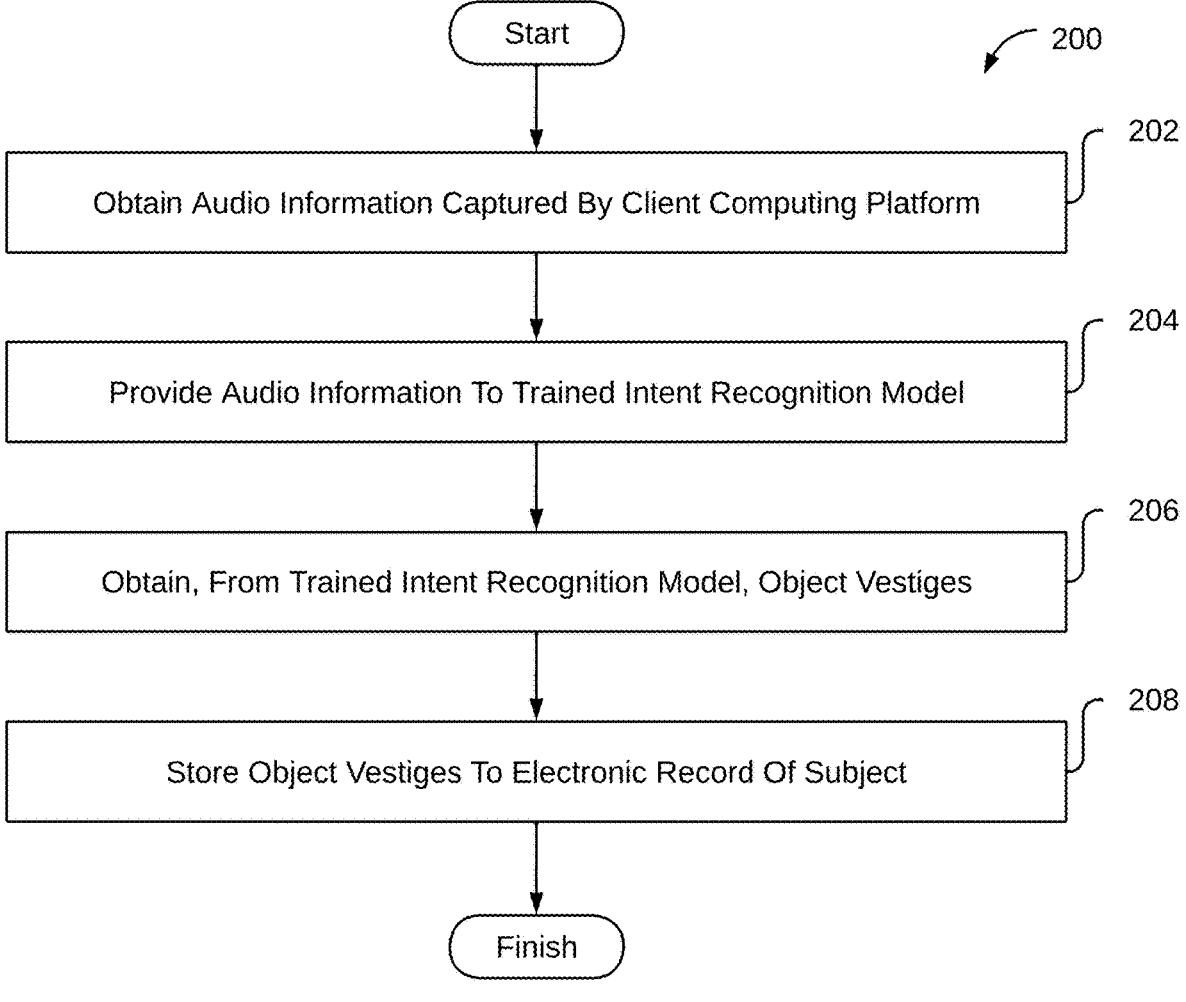
FIG. 2 illustrates a method configured to generate object vestiges based on audio information conveying natural speech, in accordance with one or more implementations.

FIG. 2 illustrates a method 200 configured to generate object vestiges based on audio information conveying natural speech, in accordance with one or more implementations. The operations of method 200 presented below are intended to be illustrative. In some implementations, method 200 may be accomplished with one or more additional operations not described, and/or without one or more of the operations discussed. Additionally, the order in which the operations of method 200 are illustrated in FIG. 2 and described below is not intended to be limiting.

In some implementations, method 200 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 200 in response to instructions stored electronically on an electronic storage medium. The one or more processing devices may include one or more devices configured through hardware, firmware, and/or software to be specifically designed for execution of one or more of the operations of method 200.

An operation 202 may include obtaining audio information captured by a client computing platform. The audio information may convey conversational speech from participants about a subject. Operation 202 may be performed by one or more hardware processors configured by machine-readable instructions including a component that is the same as or similar to information obtaining component 108, in accordance with one or more implementations.

An operation 204 may include providing the audio information to a trained intent recognition model. The trained intent recognition model may be trained to determine one or more semantic objects based on the audio information and subsequently determine object vestiges based on the one or more semantic objects. The semantic objects may indicate entities and have intent types. The intent types may include a content type and a directive type. The entities may be spoken by the participants or referred to by the participants. Operation 204 may be performed by one or more hardware processors configured by machine-readable instructions including a component that is the same as or similar to model utilization component 110, in accordance with one or more implementations.

An operation 206 may include obtaining, from the trained intent recognition model, the object vestiges. Individual ones of the object vestiges may be one of the intent types. The object vestiges of the content type may include content related the subject and the entities. The object vestiges of the directive type may include one or more values to one or more directive parameters related to the entities for external resources to initiate actions for the subject. Operation 206 may be performed by one or more hardware processors configured by machine-readable instructions including a component that is the same as or similar to model utilization component 110, in accordance with one or more implementations.

An operation 208 may include storing the object vestiges to an electronic record of the subject. Operation 208 may be performed by one or more hardware processors configured by machine-readable instructions including a component that is the same as or similar to vestige utilization component 112, in accordance with one or more implementations.

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

What is claimed is:

1. A system configured to generate object vestiges based on audio information conveying natural speech, the system comprising:

electronic storage that stores electronic records for subjects and a trained intent recognition model, wherein the trained intent recognition model is trained to determine object vestiges based on semantic objects as input, wherein the semantic objects indicate entities and have intent types, wherein the intent types include a content type and a directive type, and wherein an individual object vestige is a result caused or generated based on an individual semantic object, the result including one or both of a generation of content or a sending of a directive to an external resource; and one or more processors configured by machine-readable instructions to:

obtain audio information captured by a client computing platform, wherein the audio information conveys conversational speech from participants about a subject;

provide the audio information to the trained intent recognition model, wherein the trained intent recognition model is trained to determine one or more of the semantic objects based on the audio information and subsequently determine the object vestiges based on the one or more semantic objects, wherein the entities are spoken by the participants or referred to by the participants;

obtain, from the trained intent recognition model, the object vestiges, wherein individual ones of the object vestiges include timing information indicating times at which the entities included in the semantic objects corresponding to the object vestiges were spoken, wherein the times are based on the audio information, wherein the individual ones of the object vestiges are one of the intent types, wherein the object vestiges of:

the content type include content related to the subject and the entities, and the directive type include one or more values for one or more directive parameters related to the entities for external resources to initiate actions for the subject; and store the object vestiges to an electronic record of the subject, wherein storing the object vestiges includes grouping the object vestiges based on the timing information.

2. The system of claim 1, wherein the one or more processors are further configured by the machine-readable instructions to:

receive a request specifying one or more particular subtypes of the content types and/or one or more particular subtypes of the directive types for determining the semantic objects.

3. The system of claim 2, wherein the subtypes of the content types include a clinical note, directions, a summary, a follow up note, a letter, wherein the letter includes a referral letter, a thank you letter, an occupational note, and an approval letter.

4. The system of claim 3, wherein the subtypes of the directive types include prescription orders, device orders, imaging orders, visit scheduling, prescription modifications, device modifications, and/or scheduled visit modifications.

5. The system of claim 4, wherein the object vestiges are based on the electronic record of the subject, the subtypes of the content types, and/or the subtypes of the directive types input to the trained intent recognition model.

6. The system of claim 1, wherein the participants include a user of the client computing platform, one or more secondary users of the client computing platform, the subject, and/or a guardian of the subject.

7. The system of claim 4, wherein the one or more processors are further configured by the machine-readable instructions to:

effectuate, via the client computing platform of the user, presentation of an ordered list including the subtypes of the content types and the subtypes of the directive types that are selectable by the user, wherein determining the semantic objects is based on the selections, the electronic record of the subject, the user, and/or a purpose of the speech.

8. A system configured to train an intent recognition model to determine object vestiges based on conversational input, the system comprising:

electronic storage that stores an intent recognition model and training information, wherein the training information includes (i) audio information representing conversational speech and/or transcripts corresponding to the audio information, (ii) entities included in the audio information and/or the transcripts, (iii) intent types, and (iv) final object vestiges, wherein the intent types include a content type and a directive type; and one or more processors configured by machine-readable instructions to:

obtain the intent recognition model;

obtain the training information;

train the intent recognition model by using the audio information and/or the transcripts, the entities, and the intent types as training input, and the final object vestiges as the training outputs so that the intent recognition model is trained to determine semantic objects that indicate the entities and have one of the intent types and subsequently determine object vestiges based on the semantic objects, wherein individual ones of the object vestiges are one of the intent types and either include content related to the entities or values for directive parameters related to the entities to initiate actions, wherein an individual object vestige is a result caused or generated based on an individual semantic object, the result including one or both of a generation of content or a sending of a directive to an external resource, wherein the individual ones of the object vestiges include timing information indicating times at which the entities included in the semantic objects corresponding to the object vestiges were spoken, wherein the times are based on the audio information, and wherein the object vestiges are stored based on grouping the object vestiges based on the timing information; and store the trained intent recognition model to the electronic storage.

9. A method configured to generate object vestiges based on audio information conveying natural speech, the method comprising:

obtaining audio information captured by a client computing platform, wherein the audio information conveys conversational speech from participants about a subject;

providing the audio information to a trained intent recognition model, wherein the trained intent recognition model is trained to determine one or more semantic objects based on the audio information and subsequently determine object vestiges based on the one or more semantic objects, wherein the semantic objects indicate entities and have intent types, wherein the intent types include a content type and a directive type, wherein the entities are spoken by the participants or referred to by the participants, and wherein an individual object vestige is a result caused or generated based on an individual semantic object, the result including one or both of a generation of content or a sending of a directive to an external resource;

obtaining, from the trained intent recognition model, the object vestiges, wherein individual ones of the object vestiges include timing information indicating times at which the entities included in the semantic objects corresponding to the object vestiges were spoken, wherein the times are based on the audio information, wherein the individual ones of the object vestiges are one of the intent types, wherein the object vestiges of the content type include content related to the subject and the entities, and wherein the object vestiges of the directive type include one or more values for one or more directive parameters related to the entities for external resources to initiate actions for the subject; and storing the object vestiges to an electronic record of the subject, wherein the storing of the object vestiges includes grouping the object vestiges based on the timing information.

10. The method of claim 9, further comprising:

receiving a request specifying one or more particular subtypes of the content types and/or one or more particular subtypes of the directive types for determining the semantic objects.

11. The method of claim 10, wherein the subtypes of the content types include a clinical note, directions, a summary, a follow up note, a letter, wherein the letter includes a referral letter, a thank you letter, an occupational note, and an approval letter.

12. The method of claim 11, wherein the subtypes of the directive types include prescription orders, device orders, imaging orders, visit scheduling, prescription modifications, device modifications, and/or scheduled visit modifications.

13. The method of claim 12, wherein the object vestiges are based on the electronic record of the subject, the subtypes of the content types, and/or the subtypes of the directive types input to the trained intent recognition model.

14. The method of claim 9, wherein the participants include a user of the client computing platform, one or more secondary users of the client computing platform, the subject, and/or a guardian of the subject.

15. The method of claim 12, further comprising:
effectuating, via the client computing platform of the user, presentation of an ordered list including the subtypes of the content types and the subtypes of the directive types that are selectable by the user, wherein determining the semantic objects is based on the selections, the electronic record of the subject, the user, and/or a purpose of the speech.

16. A method to train an intent recognition model to determine object vestiges based on conversational input, the method comprising:
obtaining an intent recognition model from electronic storage, wherein the electronic storage further stores training information, wherein the training information includes (i) audio information representing conversational speech and/or transcripts corresponding to the audio information, (ii) entities included in the audio information and/or the transcripts, (iii) intent types, and (iv) final object vestiges, wherein the intent types include a content type and a directive type;
obtaining the training information;
training the intent recognition model by using the audio information and/or the transcripts, the entities, and the intent types as training input, and the final object vestiges as the training outputs so that the intent recognition model is trained to determine semantic objects that indicate the entities and have one of the intent types and subsequently determine object vestiges based on the semantic objects, wherein individual ones of the object vestiges are one of the intent types and either include content related to the entities or values for directive parameters related to the entities to initiate actions, and wherein an individual object vestige is a result caused or generated based on an individual semantic object, the result including one or both of a generation of content or a sending of a directive to an external resource, wherein the individual ones of the object vestiges include timing information indicating times at which the entities included in the semantic objects corresponding to the object vestiges were spoken, wherein the times are based on the audio information, and wherein the object vestiges are stored based on grouping the object vestiges based on the timing information; and
storing the trained intent recognition model to the electronic storage.

* * * * *